United States Patent
Liu et al.

(10) Patent No.: US 10,254,256 B2
(45) Date of Patent: Apr. 9, 2019

(54) METHOD OF PACKING CHROMATOGRAPHIC COLUMNS, PACKED CHROMATOGRAPHIC COLUMNS FOR USE AT HIGH PRESSURES AND USES THEREOF

(71) Applicants: DIONEX CORPORATION, Sunnyvale, CA (US); THERMO HYPERSIL-KEYSTONE LLC, Bellefonte, PA (US)

(72) Inventors: Xiaodong Liu, Cupertino, CA (US); Jennifer M. Nguyen, State College, PA (US); Ronald A. Sherant, Centre Hall, PA (US); Mark L. Tracy, Sunnyvale, CA (US)

(73) Assignees: Thermo Hypersil-Keystone LLC, Bellefonte, PA (US); Dionex Corporation, Sunnyvale, CA (US)

( * ) Notice: Subject to any disclaimer, the term of this patent is extended or adjusted under 35 U.S.C. 154(b) by 227 days.

(21) Appl. No.: 14/872,139

(22) Filed: Oct. 1, 2015

(65) Prior Publication Data
US 2017/0097326 A1     Apr. 6, 2017

(51) Int. Cl.
*G01N 30/56*     (2006.01)
*B01D 15/20*     (2006.01)
*G01N 30/02*     (2006.01)

(52) U.S. Cl.
CPC .......... *G01N 30/56* (2013.01); *B01D 15/206* (2013.01); *G01N 2030/027* (2013.01); *G01N 2030/565* (2013.01)

(58) Field of Classification Search
CPC ................. G01N 30/56; G01N 2030/565
See application file for complete search history.

(56) References Cited

U.S. PATENT DOCUMENTS 4,483,773 A * 11/1984 Yang .................... B01D 15/206
                                        210/198.2
6,402,958 B1 * 6/2002 Moran ................. B01D 15/206
                                       141/12

(Continued)

FOREIGN PATENT DOCUMENTS

| DE | 3334902 A1 | 4/1984 |
| GB | 2128099 B | 7/1986 |

(Continued)

OTHER PUBLICATIONS

Fekete et al. "Superficially Porous Particles: Perspectives, Practices, and Trends" Jun. 1, 2014, http://www.chromatographyonline.com/superficially-porous-particles-perspectives-practices-and-trends-0. *

(Continued)

*Primary Examiner* — Clayton E. LaBalle
*Assistant Examiner* — Dennis Hancock

(57) ABSTRACT

A method of packing a chromatography column, including: dispersing chromatographic media particles in a slurry solution to form a slurry, filling a chromatography column with the chromatographic media particles by introducing the slurry to the column and applying a pressure to pack the chromatographic media particles in the chromatography column. The slurry solution is preferably aqueous based slurry solution. The pressure is preferably applied and held substantially constant for a first period at a first pressure and is applied and held substantially constant for a second period, following the first period, at a second pressure higher than the first pressure.

12 Claims, 7 Drawing Sheets

(56) References Cited

U.S. PATENT DOCUMENTS

| | | | |
|---|---|---|---|
| 2002/0017149 A1 | 2/2002 | Maikner | |
| 2003/0150806 A1* | 8/2003 | Hobbs | B01F 13/0059 210/635 |
| 2009/0015808 A1 | 1/2009 | Owa et al. | |
| 2010/0313992 A1* | 12/2010 | Williams | B01D 15/206 141/1 |
| 2013/0193051 A1* | 8/2013 | Wirth | G01N 30/56 210/198.2 |
| 2013/0330312 A1* | 12/2013 | Greene | A61K 38/53 424/94.3 |
| 2014/0178912 A1* | 6/2014 | Liu | B01D 15/3847 435/18 |
| 2016/0332142 A1* | 11/2016 | Gu | B01D 15/3809 |

FOREIGN PATENT DOCUMENTS

| | | |
|---|---|---|
| JP | 5928660 A | 2/1984 |
| JP | 5970963 A | 4/1984 |
| JP | 63135856 A | 6/1988 |
| JP | 1176209 A | 7/1989 |
| JP | 8050123 A | 2/1996 |
| JP | 2002131300 A | 5/2002 |
| JP | 2003279553 A | 10/2003 |
| JP | 2005526974 | 9/2005 |
| JP | 2006078231 A | 3/2006 |
| JP | 2010230575 A | 10/2010 |
| JP | 2013524240 A | 6/2013 |
| WO | WO2011127044 A2 | 2/2012 |

OTHER PUBLICATIONS

Anonymous, "Instruction Sheet Packing Conditions for Self pack POROS 20 OH Media," retrieved from the internet: URL:https://tools.thermofisher.com/content/sfs/manuals/cms_041671.pdf (retrieved on Feb. 8, 2017).

Kirkland et al., "The art and science of forming packed analytical high-performance liquid chromatography columns," J. of Chromatography A, 1126(1-2), 50-57, 2006.

MacNair et al., "Ultrahigh-pressure Reversed-Phase Liquid Chromatography in Packed Capillary Columns," Anal. Chem., 69(6), 983-989, 1997.

* cited by examiner

METHOD OF PACKING CHROMATOGRAPHIC COLUMNS, PACKED CHROMATOGRAPHIC COLUMNS FOR USE AT HIGH PRESSURES AND USES THEREOF

FIELD

This invention relates to the field of liquid chromatographic columns. In particular, it relates to methods of packing of such columns that can withstand high operating pressures, especially above 1000 bar. The invention also relates to liquid chromatographic columns packed in this way and uses thereof.

BACKGROUND

Liquid chromatography (LC), e.g. high performance liquid chromatography (HPLC), is used routinely in analytical chromatography applications for determination of the quality and quantity of analytes in a variety of samples, both chemical and biological. In these chromatographic techniques, separation of a sample including a mixture of components (also termed analytes) is achieved by conveying the sample in a liquid mobile phase through a stationary phase in a column, thereby causing the sample to separate into its components due to different partitioning between the mobile and stationary phases of each of the components (i.e. the components have different partition coefficients). The stationary phase is most commonly in the form of a bed of particles packed within the column. In order to provide high resolution and throughput of samples, high operating pressures are employed in HPLC of typically up to 600 bar.

In order to deliver ultra-high resolution and/or ultra-fast throughput analysis, which is important for quality of data and cost of analysis, ultra high performance liquid chromatography (UHPLC) has been developed, employing the benefits of low system dispersion and ultra-high system operating pressure (typically greater than 1000 bar). UHPLC columns are a critical element for UHPLC solutions. To fully utilize the capability of a UHPLC instrument to achieve ultra-high resolution, ultra-high throughput analysis, the column is typically packed with stationary phase media including small particles, usually smaller than 2 μm (e.g. 1.5 μm). These particles can be totally porous (i.e. bulk porous), superficially porous, or non-porous and the particles may be surface modified for particular applications. Such demanding operating conditions (high pressure and/or high linear velocity) require that the separation column has excellent bed stability.

Traditionally, HPLC columns are packed in a process using one or more organic solvents (herein "solvent packing"). However, there are some drawbacks associated with this approach noted by the inventors. Firstly, the inventors have found that solvent packing often fails to provide HPLC columns that can be operated under 1300 bar pressure or higher, thereby limiting the usage of such pressures (e.g. 1500 bar) in UHPLC (e.g. in the THERMO SCIENTIFIC® VANQUISH® H UHPLC system). Secondly, most organic solvents are to some extent toxic and/or flammable, thus imposing health and safety hazards on operators and pollution on the environment. Thirdly, the use of organic solvents is expensive due to costs associated with the manufacturing process and the required waste treatment.

SUMMARY

According to a first aspect, there is provided a method of column packing including using aqueous solutions, preferably for slurry making and/or column packing under a liquid pressure, which addresses the above drawbacks of the prior art. Compared to organic solvent based packing methods, the aqueous based method has been found capable of yielding improved column stability (ruggedness) at operating pressures greater than 1000, or greater than 1300 bar, improved separation performance and improved reproducibility. The aqueous packing method has been found to provide an improved production yield over a solvent based method. For example, an aqueous packing method can provide a 90% yield compared to 50% for a solvent based method. The performance improvements include reduced peak tailing and higher separation efficiency. These benefits are accompanied by greatly reduced solvent consumption in the packing process (e.g. up to 95-100% reduction in solvent usage).

According to a second aspect, there is provided a method of column packing including a multiple pressure stage packing method. Again, performance improvements have been found to include improved column ruggedness, reduced peak tailing and improved separation efficiency.

The invention provides methods to pack LC columns that can withstand an operating pressure up to 600-bar for HPLC, as well as up to 1500-bar for UHPLC, using the aqueous based packing and/or multiple pressure stage packing methods. The invention most preferably provides methods of column packing including both aspects of using aqueous solutions and multiple pressure stages.

According to embodiments of the invention, in the first aspect, there is provided a method of packing a chromatography column, including:

dispersing chromatographic media particles in an aqueous based slurry solution to form a slurry;

filling the chromatography column with the chromatographic media particles by introducing the slurry to the column; and applying a pressure to pack the chromatographic media particles in the chromatography column.

The aqueous based slurry solution is preferably 100% water, or at least 90%, or at least 95%, or at least 99%, by weight water. The aqueous based slurry solution can contain organic solvent(s) in an amount not more than 100 parts by weight, not more than 50 parts by weight, or not more than 40 parts by weight, or not more than 30 parts by weight, or not more than 20 parts by weight, or not more than 10 parts by weight, or not more than 5 parts by weight, or not more than 1 part by weight organic solvent(s), based on 100 parts by weight of water.

The aqueous based slurry solution preferably further includes, based on 100 parts by weight of water:

0-50, or 0-40, or 0-30, or 0-20, or 0-10, or 0-5, or 0-1, parts by weight of surfactant;

0-50, or 0-40, or 0-30, or 0-20, or 0-10, or 0-5, or 0-1, parts by weight of electrolyte or salt (other than ionic surfactant);

0-100, or 0-50, or 0-30, or 0-20 or 0-10 or 0-5 or 0-1, parts by weight of acid;

0-100, or 0-50, or 0-30, or 0-20 or 0-10 or 0-5 or 0-1, parts by weight of base.

The applied pressure preferably includes a pressure of at least 500 bar, or at least 800 bar, or at least 1000 bar, or at least 1300 bar, or at least 1500 bar, or at least 2000 bar for a period of time.

The pressure is preferably applied and held substantially constant for a first period at a first pressure and is applied and held substantially constant for a second period, following the first period, at a second pressure higher than the first pressure.

According to embodiments of the invention, in the second aspect, there is provided a method of packing a chromatography column, including: dispersing chromatographic media particles in a slurry solution to form a slurry; filling the chromatography column with the chromatographic media particles by introducing the slurry to the column; and applying a pressure to pack the chromatographic media particles in the chromatography column, wherein the pressure is applied and held substantially constant for a first period at a first pressure and is applied and held substantially constant for a second period, following the first period, at a second pressure higher than the first pressure.

The first pressure is preferably in a range from 100-1500 bar, or 100-1300 bar, or 100 to 1000 bar, or 300 to 1000 bar, or 500 to 1000 bar; and the second pressure is preferably in a range from 1500 to 6000 bar, or 1500 to 5000 bar, or 1500 to 4000 bar, or 1500 to 3000 bar. The first pressure is preferably in a range from 100-1500 bar; and the second pressure is preferably in a range from 1500 to 4000 bar or 1500 to 4000 bar.

The first period is preferably in a range from 0.1-100 hours, or 0.2 to 50 hours and the second period is preferably in a range from 0.1-100 hours, or 0.2 to 50 hours.

The column preferably has an internal diameter from 10 µm to 5 mm, or from 100 µm to 5 mm; and the column preferably has a length from 20 mm to 10,000 mm, or from 20 mm-1,000 mm. The chromatographic media particles preferably have a median particle diameter of 1 to 5 µm and preferably are totally porous or superficially porous.

The invention in another aspect provides a liquid chromatography column for operation at liquid pressures of at least 500 bar, or at least 1000 bar, or at least 1300 bar or at least 1500 bar, wherein chromatographic media particles have been packed into the column from an aqueous based slurry solution. The packing of the column is preferably according to the first aspect of the invention.

The invention in yet another aspect provides a liquid chromatography column for operation at liquid pressures of at least 500 bar, or at least 1000 bar, or at least 1300 bar or at least 1500 bar, wherein chromatographic media particles have been packed into the column from a slurry solution under an applied pressure that is substantially constant for a first period at a first pressure and is and held substantially constant for a second period, following the first period, at a second pressure higher than the first pressure. The packing of the column is preferably according to the second aspect of the invention.

BRIEF DESCRIPTION OF THE DRAWINGS

The accompanying drawings, which are incorporated herein and constitute part of this specification, illustrate presently preferred embodiments of the invention, and, together with the description, serve to explain features of the invention.

FIG. 4a shows column performance results before and after the robustness test (chromatogram a and chromatogram b, respectively) on a 50×2.1 mm column packed with Media 1 (1.5 µm superficially porous silica based C18) particles at 820 bar (Example 3) using aqueous based packing methods. Note that chromatogram b was shifted upward on the y-axis for purpose of illustrating the relative differences in peak shape to chromatogram b.

FIG. 4b shows column performance results before and after the robustness test (chromatogram a and chromatogram b, respectively) on a 50×2.1 mm column packed with Media 1 (1.5 µm superficially porous silica based C18) particles at 2400 bar (Example 4) using aqueous based packing methods. Note that chromatogram b was shifted upward on the y-axis for the purpose of comparing possible differences in peak shapes with chromatogram a.

FIG. 6 shows column performance results before and after the robustness test (chromatogram a and chromatogram b, respectively) on a 200×2.1 mm column packed with Media 2 (1.9 µm porous silica based C18) particles using a 2-stage aqueous based packing method at 2400 bar (Example 5 above). Note that chromatogram b was shifted upward on the y-axis for the purpose of comparing possible differences in peak shapes with chromatogram a.

FIG. 7a shows column performance results before and after robustness testing (chromatogram a and chromatogram b, respectively) on a 150×2.1 mm column packed with Media 2 (1.9 µm porous silica based C18) particles at 2400 bar using a solvent based packing method of Example 6. Note that chromatogram b was shifted upward on the y-axis for the purpose of comparing possible differences in peak shapes with chromatogram a.

FIG. 7b shows column performance results before and after robustness testing (chromatogram a and chromatogram b, respectively) on a 150×2.1 mm column packed with Media 2 (1.9 µm porous silica based C18) particles at 2400 bar using a 2-stage aqueous based method of Example 7. Note that chromatogram b was shifted upward on the y-axis for the purpose of comparing possible differences in peak shapes with chromatogram a.

DETAILED DESCRIPTION

Figure 1:
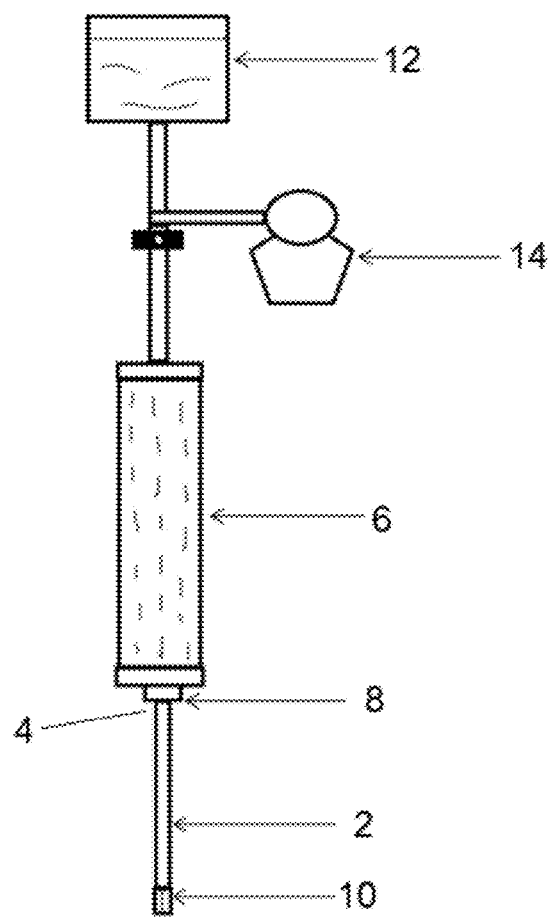
FIG. 1 shows schematically an apparatus for implementing a packing process.

Various preferred features, embodiments and examples of the invention will now be described in more detail.

The invention in the first aspect preferably includes dispersing chromatographic media particles in a slurry solution containing at least 50% by weight water. A weight of chromatographic media particles sufficient to fill the column is dispersed. A slurry is thereby formed. The slurry solution preferably contains at least 60%, or at least 70%, or at least 80%, more preferably at least 90%, or at least 95%, or at least 99%, by weight water. The water is preferably de-ionized (D.I.) water. The slurry solution optionally but preferably includes one or more additives. The additives may be selected from surfactant(s), electrolyte(s) such as salt(s), acid(s) and/or base(s). The slurry solution optionally may contain organic solvent(s), based on 100 parts by weight of water, preferably in an amount not more than 100 parts by weight, not more than 50 parts by weight, or not more than 40 parts by weight, or not more than 30 parts by weight, or not more than 20 parts by weight, more preferably not more than 10 parts by weight, or not more than 5 parts by weight, or not more than 1 part by weight, by weight organic solvent(s).

In some embodiments, the slurry solution can include 100% by weight water. It will therefore be appreciated that the term solution is being used in this context not in its strict sense only to mean water containing one or more components but also to mean pure (100%) water in some embodiments. In certain preferred embodiments, the slurry solution can include: 90-100% by weight water and 0-10% by weight of solvent.

In addition to the water and optional solvent, the slurry solution can further include (based on 100 parts by weight of water):

0-50, preferably 0-40, more preferably 0-30, most preferably 0-20 or 0-10 or 0-5 or 0-1, parts by weight of surfactant;

0-50, preferably 0-40, more preferably 0-30, most preferably 0-20 or 0-10 or 0-5 or 0-1, parts by weight of electrolyte or salt (other than ionic surfactant);

0-100, preferably 0-50, more preferably 0-30, most preferably 0-20 or 0-10 or 0-5 or 0-1, parts by weight of acid; and 0-100, preferably 0-50, more preferably 0-30, most preferably 0-20 or 0-10 or 0-5 or 0-1, parts by weight of base.

Most preferably a surfactant is present, e.g. 0.1-50, preferably 0.1-40, more preferably 0.1-30, most preferably 0.1-20 or 0.1-10 or 0.1-5 or 0.1-1, parts by weight of surfactant.

One preferred slurry solution, and/or packing solution, composition includes:
at least 90%, by weight water; and based on 100 parts by weight of water:
0-10 parts by weight of organic solvent(s);
0-10 parts by weight of surfactant (especially 0.1-10, parts by weight of surfactant);
0-10 parts by weight of electrolyte or salt;
0-10 parts by weight of acid; and
0-10 parts by weight of base.

Another preferred slurry solution, and/or packing solution, composition includes:
at least 95%, by weight water; and based on 100 parts by weight of water:
0-5 parts by weight of organic solvent(s);
0-5 parts by weight of surfactant (especially 0.1-1, parts by weight of surfactant);
0-5 parts by weight of electrolyte or salt;
0-5 parts by weight of acid; and
0-5 parts by weight of base.

The solvent is an organic solvent and is not particularly limited in type. Preferably the solvent includes one or more solvents selection from the following list (but is not limited to these): methanol, ethanol, iso-propanol, acetone, acetonitrile, methylene chloride, chloroform, hexane(s), heptanes (s), cyclohexane, etc.

The additive(s) can be, for example, any one or more additive(s) selected from: acids, bases, surfactants, salts, or any combination of these substances.

Preferred acid(s) include(s): acetic acid, formic acid, methane sulfonic acid, sulfuric acid, phosphoric acids, nitric acid, and citric acid, trifluoroacetic acid (TFA), etc.

Preferred base(s) include(s): sodium hydroxide, potassium hydroxide, ammonium hydroxide, tetramethyl ammonium hydroxide, tetrabutylammonium hydroxide, sodium, potassium carbonate, etc.

Preferred surfactant(s) include(s): polyethylene glycol, which may have different molecular weights, sodium decyl sulfate, sodium dodecyl sulfate, sodium dodecyl sulfonate, alkyl ethoxylates, Triton X-100 (polyethylene glycol p-(1, 1,3,3-tetramethylbutyl)-phenyl ether), cetyltrimethylammonium chloride, cetyltrimethylammonium bromide. The surfactant(s) may be anionic, cationic, non-ionic and/or amphoteric surfactant(s).

Preferred salts include NaCl, KCl, sodium and/or potassium phosphates, sodium and/or potassium sulphates, sodium acetate, sodium formate, etc.

It can therefore be seen that the invention provides a column packing method using an aqueous based slurry solution and packing solution. The slurry solution and packing solution can each independently be:
pure water;
an aqueous solution containing additives as described;
a mixture of water and solvent, wherein the water content is at least 50% by weight of the mixture; or
a mixture of water and solvent, wherein the water content is at least 50% by weight of the mixture, further containing additives as described.

The invention in the second aspect, which is preferably combined with the first aspect, preferably includes a first packing stage (or "first pack") that is performed at a first pressure followed by a second packing stage (or "second pack") that is performed at a second pressure higher than the first pressure. Thus, the invention provides a two stage, or at least two stage packing process. The process is illustrated in one embodiment by reference to FIG. 1. Prior to the packing at pressure, e.g. the first packing stage, the method preferably includes attaching one end (4) of the empty column body (2), such as an HPLC or UHPLC column, to a packing reservoir (6), optionally via an adapter (8), the column having an end-fitting (10) (preferably together with a media support, such as a frit) fitted on the other end to retain the media in the column. This arrangement is referred to herein as a packing station or the first packing station (where two or more such arrangement are used). The column is preferably positioned substantially vertically with the end-fitting (10) on the lower end and the packing reservoir (6) attached to the higher end (4). The method preferably further includes transferring a prepared slurry containing chromatographic media particles, preferably but not necessarily a slurry as described herein, into the packing reservoir (6) followed by topping with a solution, for example further slurry solution (e.g. the solution alone, substantially without chromatographic media particles), which is herein referred to as "packing solution" or "push solution". The push solution may be fed to the packing reservoir (6) from a further reservoir (12). The slurry from the packing reservoir thereby fills the column (2). Alternatively, the slurry could be formed within the packing reservoir to dispense with the slurry transfer process. Both the slurry solution containing the media and the packing solution are preferably aqueous based, i.e. containing at least 50% by weight water, and preferably the aforesaid amounts of water and other components. However, the two stage, or at least two stage, packing process may also be beneficial with solvent based slurry column packing.

Then the method preferably proceeds by applying pressure, typically by means of a pump (14), to the slurry in the column (2) and reservoir (6) to start packing (i.e. the first packing stage). In this way, the slurry solution is pumped through the column and the media particles from the slurry are retained in the column by a media support, such as a frit, on the other end of the column (10), i.e. the other end to the end through which the slurry is introduced. The pressure is preferably applied in the first packing stage with a pressure ramp, including slow to fast pressure ramping. As the slurry with media particles is packed into the column, the packing solution then applies further pressure to the particles. The pressure is preferably, after ramping to reach a first pressure, kept at the first pressure for a first packing time. The first pressure is preferably in the range of 100-1500 bar, or 100-1300 bar, more preferably 100 to 1000 bar, or 300 to 1000 bar, or 500 to 1000 bar. In some embodiments, the first packing pressure is in the range of 600 to 900 bar, or 700 to 900 bar. The first packing time (that the first pressure is applied for) is preferably in the range 0.1-100 hours, more preferably 0.2 to 50 hours, most preferably 0.3 to 48 hours.

Following the first packing stage, especially if the packing reservoir cannot withstand the higher pressure of the second packing stage, preferably the column is disconnected from the packing reservoir and moved to a second packing station where higher pressures can be applied, wherein the column is connected directly to a pump and source of push solution for the second stage. The pump used for the second packing station could be the same as, or different to, the pump used for the first packing stage. Before moving the column to the other packing station for the second stage, the pressure is relieved from the column. Then the column can be moved to the other packing station for further packing. However, if the packing reservoir can withstand higher pressures, e.g. UHPLC pressures used in the second packing stage, the second pressure could be applied at the first stage and preferably without dropping the pressure substantially.

The method preferably proceeds by applying a second pressure (preferably by increasing from the first pressure to reach the second pressure if the packing is performed on one station), and keeping at the second pressure for a second packing time. The second pressure is preferably in the range of 200-6000 bar, more preferably 200 to 5000 bar, or 200 to 4000 bar, most preferably 500 to 4000 bar or 500 to 3000 bar. In some embodiments, the second pressure is preferably in the range of 1500-6000 bar, more preferably 1500 to 5000 bar, or 1500 to 4000 bar, most preferably 1500 to 4000 bar or 1500 to 3000 bar. In some embodiments, the second packing pressure is in the range of 2000 to 4000 bar, or 2000 to 3000 bar. The second packing time (that the second pressure is applied for) is preferably in the range 0.1-100 hours, more preferably 0.2 to 50 hours. Preferably, the second packing pressure is greater than the maximum operating pressure of the column in use. The second stage has been found to play a significant role in stabilizing the packed bed of media particles against repeated use at UHPLC conditions. Optionally, a third packing stage, etc., may be performed at a third packing pressure, preferably at still higher pressure than the previous (second) stage, for a third packing time etc. The third packing pressure may be in the range 300-6000 bar, or 500-5000 bar, or 500 to 4000 bar, for example. The packing steps can be performed on the same packing station or different packing stations. The packing process (first and second stages) may be performed at room or ambient temperatures, up to about 80 degrees C.

After packing, the column can be fitted with a second end fitting (preferably together with a media support, such as a frit) at it other end to the first fitting and tested for chromatography performance. The packed column is preferably subjected to washing before use.

The HPLC and UHPLC column products produced by the methods of the invention can be operated under pressures from 400 to 2000 bar, preferably at operating pressures greater than 1000, or greater than 1300, or greater than 1500 bar. The column body is typically tubular and typical column inner diameters that can be packed can be from 10 µm to 5 mm, or from 100 µm to 5 mm, or from 1 mm to 5 mm. The typical column lengths that can be packed can be from 20 mm to 10,000 mm, or from 20 mm-1,000 mm, or from 20 mm-500 mm, or from 20 mm-200 mm, or from 50 mm-150 mm. Preferably, the column dimension may be any combination of x mm inner diameter by y mm length, wherein x=0.05 to 10 mm and y=20 to 1000 mm. The column body is typically a steel column, usually stainless steel.

The chromatographic media is preferably particulate media, wherein particles of the media are typically and preferably substantially spherical but may be irregular in shape in some embodiments. The particles preferably have a narrow size distribution.

The media particles can be porous (totally, i.e. bulk, porous), superficially porous, or nonporous particles. The particles can be silica and/or metal oxide. The particles are preferably selected from any one or more of: silica, silica-organo hybrid, or organic polymer particles.

In certain examples, the particles are essentially "monodisperse" or essentially "homodisperse", which indicates that the particle size of the majority of the particles (e.g., 80, 90 or 95% of the particles) does not vary substantially (e.g., not more than 10%) below or above the median particle size ($D_{50}$). In an exemplary monodisperse particle population, 90% of the particles have an average particle size of between about $0.9 \times D_{50}$ and about $1.1 \times D_{50}$. This is advantageous for chromatographic applications. Whilst monodispersed particles are preferred, particles with a broader particle size distribution may be useful in many applications.

The particles of the chromatographic media are typically microparticles, preferably 0.1 µm or larger in median particle diameter. More preferably, the particles are from 0.1 to 100 µm, or 0.1 to 50 µm or 0.1 to 20 µm in diameter, or still more preferably 0.1 to 10 µm, or 0.1 to 5 µm in diameter, or 0.1 to 3 µm in diameter, or even more preferably 0.1 to 2 µm in diameter, especially 0.2 to 5 µm, or 0.2 to 3 µm, or 0.2 to 2 µm, or 0.5 to 5 µm, or 0.5 to 3 µm, or 0.5 to 2 µm, or 1 to 5 µm, or 1 to 3 µm or most preferably 1 to 2 µm in diameter.

The particles of the chromatographic media may be porous (including totally porous, i.e. bulk porous, or superficially porous) or non-porous particles.

When porous particles are used as the chromatographic media, the pores of the particles can be of any size. The nominal pore size is typically measured as a diameter in units of angstroms ($10^{-10}$ m, Å). A pore size distribution (PSD) is calculated from adsorption data using the BJH (Barrett Joyner-Halenda) method and the average pore size ($W_{BJH}$) is defined as the maximum of the PSD. In one example, the average size or diameter of the pores is between about 1 and about 5000 Å, especially between about 50 and about 5000 Å. In another example, the average diameter of the pores is between about 10 and about 5000 Å, between about 10 and about 4000 Å, between about 10 and about 3000 Å, between about 10 and about 2000 Å, between about 10 and about 1000 Å, between about 10 and about 800 Å, between about 10 and about 600 Å, between about 10 and about 500 Å, between about 10 and about 400 Å, between about 10 and about 300 Å, between about 10 and about 200 Å, between about 10 and about 100 Å, between about 20 and about 2000 Å, between about 20 and about 1000 Å, between about 20 and about 500 Å, between about 20 and about 300 Å, between about 20 and about 200 Å, between about 20 and about 100 Å, between about 30 and about 2000 Å, between about 30 and about 1000 Å, between about 30 and about 500 Å, between about 30 and about 300 Å, between about 30 and about 200 Å, between about 30 and about 100 Å, between about 40 and about 2000 Å, between about 40 and about 1000 Å, between about 40 and about 500 Å, between about 40 and about 300 Å, between about 40 and about 200 Å, between about 40 and about 100 Å, between about 50 and about 2000 Å, between about 50 and about 1000 Å, between about 50 and about 500 Å, between about 50 and about 300 Å, between about 50 and about 200 Å, between about 50 and about 100 Å, between about 60 and about 2000 Å, between about 60 and about 1000 Å, between about 60 and about 500 Å, between about 60 and about 300 Å, between about 60 and about 200 Å, between about 60 and about 100 Å, between about 70 and about 2000 Å, between about 70 and about 1000 Å, between about 70 and about 500 Å, between about 70 and about 300 Å, between about 70 and about 200 Å, between about 70 and about 100 Å, between about 80 and about 2000 Å, between about 80 and about 1000 Å, between about 80 and about 500 Å, between about 80 and about 300 Å, between about 80 and about 200 Å, between about 100 and about 200 Å, between about 100 and about 300 Å, between about 100 and about 400 Å, between about 100 and about 500 Å, between about 200 and about 500 Å or between about 200 and about 600 Å. Preferably, the average pore size diameter is between about 30 and about 2000 Å, more preferably between about 80 and about 1000 Å. Most preferably, the average pore size diameter is between about 80 and about 300 Å.

The (BET) specific surface area of the porous particulate chromatographic media is typically between about 0.1 and about 2,000 $m^2/g$, most typically between about 0.1 and about 1,000 $m^2/g$. For example, the specific surface area of the particulate material is between about 1 and about 1,000 $m^2/g$, between about 1 and about 800 $m^2/g$, between about 1 and about 600 $m^2/g$, between about 1 and about 500 $m^2/g$, between about 1 and about 400 $m^2/g$, between about 1 and about 200 $m^2/g$ or between about 1 and about 100 $m^2/g$. In another example, the specific surface area of the material is between about 10 and about 1,000 $m^2/g$, between about 10 and about 800 $m^2/g$, between about 10 and about 600 $m^2/g$, between about 10 and about 500 $m^2/g$, between about 10 and about 400 $m^2/g$, between about 10 and about 200 $m^2/g$ or between about 10 and about 100 $m^2/g$. In another example, the specific surface area of the material is between about 50 and about 1,000 $m^2/g$, between about 50 and about 800 $m^2/g$, between about 50 and about 600 $m^2/g$, between about 50 and about 500 $m^2/g$, between about 50 and about 400 $m^2/g$, between about 50 and about 200 $m^2/g$ or between about 50 and about 100 $m^2/g$. Preferably, the specific surface area of the particulate material is between about 1 and about 500 $m^2/g$, or between about 10 and about 500 $m^2/g$ (especially between about 50 and about 500 $m^2/g$). In another example, the specific surface area more preferably is between about 10 and about 100 $m^2/g$.

For non-porous particles, the specific surface area preferably is between about 0.5-10 $m^2/g$. For non-porous particles, the median particle diameter is preferably from 0.1 to 5 μm, preferably 0.1 to 2 μm, more preferably 0.1 to 2 μm.

The column packing methods of this invention can be applied to different types of particulate chromatographic media, including but not limited to any of the following:
Reversed-phase media (hydrophobic surface)
HILIC or normal phase media (hydrophilic surface)
Ion-exchange phase media (charged surface)
Mixed-mode phase media (hydrophobic (or hydrophilic) combined with charged surface.

The liquid chromatography column produced by the invention preferably has high robustness to repeated use at high pressure and ultra high pressure. The column efficiency (Number of theoretical plates per meter, N/m) preferably changes by less than 10% after a robustness test in which the pressure applied to the column is oscillated between 0 bar for 2 min and 1500 bar for 3 min 100 times. The peak tailing factor preferably changes (typically increases) by less than 15% after the robustness test. The backpressure preferably changes (typically increases) by less than 10% after the robustness test.

EXAMPLES

General Procedure

An exemplary general procedure for packing columns is now described, which is followed by specific examples. These are non-limiting on the scope of the invention.

Preferably, totally porous or superficially porous particulate chromatographic media is used for packing.

Step 1:

Assemble the column body with a frit, such as a 0.2 μm or 0.5 μm frit, and an end fitting on one end, and attach the other end to an adapter connected to a column packing reservoir which is connected to a packing pump. The column is positioned vertically with the end fitting on the lower end of the column and the adapter and column packing reservoir on the higher end. The packing pump can suitably be a constant pressure or a constant flow pump. The packing pump is equipped with a bottle or reservoir containing a packing or push solution, which can be aqueous based, or organic solvent based, such as methanol, iso-propanol, acetone, acetonitrile, methylene chloride, chloroform, hexane, heptanes, and others, as well as a mixture of any two or more of these. However, in accordance with aspects of this invention, it is preferred to use an aqueous based push solution such as one of: pure water; aqueous solution containing additives such as, surfactant, salt, acid, and/or base; a mixture of water and solvent (wherein water is at least 50% by weight and preferably at least 90% by weight); or a mixture of solvent and aqueous solution containing additives such as acid, base, surfactant, and/or salt (wherein water is at least 50% by weight and preferably at least 90% by weight of the mixture).

Step 2:

Measure an appropriate amount of chromatographic media particles, i.e. an amount to fill the column. The particles can be porous, superficially porous, or nonporous. The particles should be selected from pure silica, organo-silica hybrid, metal-oxide, organic polymer based particles. The particle size should be from 0.5 to 10 μm, preferably 1 to 5 μm, and most preferably 1 to 2 μm. The media particles can then be dispersed in a slurry solution until a slurry of uniformity dispersion is achieved. The slurry solution can be aqueous based, or organic solvent based, such as methanol, iso-propanol, acetone, acetonitrile, methylene chloride, chloroform, hexane, heptanes, and others, as well as a mixture of any two or more of these. However, in accordance with aspects described herein, it is preferred to use an aqueous based push solution such as one of: pure water; aqueous solution containing additives such as, surfactant, salt, acid, and/or base; a mixture of water and solvent (wherein the mixture is at least 50% by weight water and preferably at least 90% by weight water); or a mixture of solvent and aqueous solution containing additives such as acid, base, surfactant, and/or salt (wherein the mixture is at least 50% by weight water and preferably at least 90% by weight water).

Step 3:

Pour the resulting slurry from step 2 into the packing reservoir with the empty column attached at the bottom of the packing reservoir. The slurry of particles drops by gravity into the empty column at this stage (i.e., before pumping pressure is applied). The packing reservoir can then be closed with a cap.

Step 4—First Packing Stage:

Push the push solution through the packing reservoir and the column packing with the packing pump controlled to apply a selected first pressure and keep the pressure constant at the selected pressure for a certain period of time. To form a well-packed bed, a selected pressure in the 100-1500 bar range is applied. The selected pressure is reached by pressure ramping, which can be a sudden or gradual pressure change, and is then followed by holding the reached selected pressure for a period in the range from 20 min to 48 hours (preferably 2 to 25 hours, or 5 to 10 hours, e.g. about 15 hours).

Step 5—Second Packing Stage:

Apply a second, higher pressure to push the push solution through the packing reservoir and the column packing with the packing pump. This has been found to further stabilize the packed bed in the column. The second, higher pressure should be in the 200-4000 bar range and is reached by increasing the packing pressure to the higher pressure, followed by keeping the pressure constant at the second higher pressure for a certain period of time, in the range from 20 min to 48 hours (preferably 0.5 to 25 hours and especially 0.5 to 5 hours, or 0.5 to 1 hour).

Step 6:

Release the pressure, detach the column and put a frit and end-fitting on the other end of the column.

Step 7:

Wash the packed column with a washing solvent or solution, for example with acetonitrile, and then preferably with mobile phase prior to use and/or testing.

In the following examples, two types of chromatographic media were packed into columns:

Media 1: 1.5 µm superficially porous silica-based C18 particles; and

Media 2: 1.9 µm totally porous silica-based C18 particles.

Example 1—Packing Media 1 into a 100×2.1 mm Column Using an Aqueous Based Packing Method 0.45 g Media 1 particles were suspended in 20 mL of a slurry solution (0.5:0.5:99, sodium dodecyl sulfate/ethanol/water by weight ratio). The resulting slurry was poured into the packing reservoir attached to a 100×2.1 mm column blank fitted with a first frit and end fitting at its lower end. After closing the reservoir cap, the pressure was ramped to the 600-1000 bar range with water as the push solution. After keeping the packing pressure at the same pressure (800 bar) for 2 to 24 hours, the packing pressure was increased to the 1500-3000 bar range and kept at the same pressure (2400 bar) for 0.5 to 24 hours. The pressure was released and a second frit and end-fitting were assembled on the column in place of the packing reservoir. The column was washed with 100% acetonitrile for 20 column volumes. The column performance was tested and the test results are illustrated in chromatogram a of FIG. 3a (chromatographic performance). The column performance was also tested before and after subjecting the column to a robustness test which is illustrated in chromatograms a and b, respectively, of FIG. 5 (robustness).

Example 2—Packing Media 1 into a 100×2.1 mm Column Using a Solvent Based Packing Method 0.45 g Media 1 particles were suspended in 20 mL of a slurry solution (10:90, methanol/chloroform by weight ratio). The resulting slurry was poured into the packing reservoir attached to a 100×2.1 mm column blank fitted with a first frit and end fitting at its lower end. After closing the reservoir cap, the pressure was ramped to the 600-1000 bar range with methanol as the push solution. After keeping the packing pressure at the same pressure (800 bar) for 2 to 24 hours, the packing pressure was increased to the 1500-3000 bar range and kept at the same pressure (2400 bar) for 0.5 to 24 hours. The pressure was released and a second frit and end-fitting were assembled on the column in place of the packing reservoir. The column was washed with 100% acetonitrile for 20 column volumes. The column performance was then tested and the test results are illustrated in chromatogram b of FIG. 3.

The details of the performed chromatographic evaluation (column performance test) and column robustness evaluation are given below.

Example 3—Packing Media 1 into a 50×2.1 mm Column Using an Aqueous Based Packing Method at 820 Bar 0.25 g Media 1 particles were suspended in 20 mL of a slurry solution (0.25:0.25:95.5, sodium dodecyl sulfate/ethanol/water by weight ratio). The resulting slurry was poured into the packing reservoir attached to a 50×2.1 mm column blank. After closing the reservoir cap, the pressure was ramped to the 600-1000 bar range with water as the push solution. After keeping the packing pressure at the same pressure (820 bar) for 2 to 24 hours (in this example 15 hours), the pressure was released and a frit and end-fitting were assembled on the column in place of the packing reservoir. The column was washed with 100% acetonitrile for 20 column volumes. The column performance was also tested before and after subjecting the column to a robustness test which is illustrated in chromatograms a and b, respectively, of FIG. 4a.

Example 4—Packing Media 1 into a 50×2.1 mm Column Using an Aqueous Based Packing Method at 2400 Bar 0.25 g Media 1 particles were suspended in 20 mL of a slurry solution (0.25:0.25:99.5, sodium dodecyl sulfate/ethanol/water by weight ratio). The resulting slurry was poured into the packing reservoir attached to a 50×2.1 mm column blank. After closing the reservoir cap, the pressure was ramped to the 600-1000 bar range with water as the push solution. After keeping the packing pressure at the same pressure (800 bar) for 2 to 24 hours (in this example 15 hours), the packing pressure was increased to the 1500-3000 bar range and kept at the same pressure (2400 bar) for 0.5 to 24 hours (in this example 1 hour). Then the pressure was released and a frit and end-fitting were assembled on the column. The column was washed with 100% acetonitrile for 20 column volumes. The column performance was also tested before and after subjecting the column to a robustness test which is illustrated in chromatograms a and b, respectively, of FIG. 4b.

Example 5—Packing Media 2 into a 200×2.1 mm Column at 2400 Bar Using a 2-Stage Aqueous Based Packing Method 0.60 g Media 2 particles were suspended in 20 mL of a slurry solution (0.5:0.25:99.25, sodium dodecyl sulfate/ethanol/water by weight ratio). The resulting slurry was poured into the packing reservoir attached to a 200×2.1 mm column blank. After closing the reservoir cap, the pressure was ramped to the 600-1000 bar range with water as the push solution. After keeping the packing pressure at the same pressure for 2 to 24 hours (15 hours), the packing pressure was increased to the 1500-3000 bar range and kept at the same pressure for 0.5 to 24 hours (1 hour). Then the pressure was released and a frit and end-fitting were assembled on the column. The column was washed with 100% acetonitrile for 20 column volumes. The column performance was also tested before and after subjecting the column to a robustness test which is illustrated in chromatograms a and b, respectively, of FIG. 6.

Example 6—Packing Media 2 into a 150×2.1 mm Column at 2400 Bar Using a 2-Stage Solvent Based Packing Method 0.42 g Media 2 particles were suspended in 20 mL of a slurry solution (10:90, methanol/chloroform by weight ratio). The resulting slurry was poured into the packing reservoir attached to a 150×2.1 mm column blank. After closing the reservoir cap, the pressure was ramped to the 600-1000 bar range with methanol as the push solution. After keeping the packing pressure at the same pressure for 2 to 24 hours, the packing pressure was increased to the 1500-3000 bar range and kept at the same pressure for 0.5 to 24 hours. Then the pressure was released and a frit and end-fitting were assembled on the column. The column was washed with 100% acetonitrile for 20 column volumes. The column performance was also tested before and after subjecting the column to a robustness test which is illustrated in chromatograms a and b, respectively, of FIG. 7a.

Example 7—Packing Media 2 (1.9 μm Totally Porous Silica Based C18) Particles into 150×2.1 mm Column at 2400 Bar Using a 2-Stage Aqueous Based Packing Method 0.42 g Media 2 particles were suspended in 20 mL of a slurry solution (0.5:0.25:97.25, sodium dodecyl sulfate/ethanol/water by weight ratio). The resulting slurry was poured into the packing reservoir attached to a 150×2.1 mm column blank. After closing the reservoir cap, the pressure was ramped to the 600-1000 bar range with water as the push solution. After keeping the packing pressure at the same pressure for 2 to 24 hours, the packing pressure was increased to the 1500-3000 bar range and kept at the same pressure for 0.5 to 24 hours. Then the pressure was released and a frit and end-fitting were assembled on the column. The column was washed with 100% acetonitrile for 20 column volumes. The column performance was also tested before and after subjecting the column to a robustness test which is illustrated in chromatograms a and b, respectively, of FIG. 7b.

Chromatographic Evaluation

Column Performance Test

The column performance was assessed with a neutral hydrophobic probe (o-xylene) for efficiency and peak tailing factor. The chromatographic conditions were as given below:

Column: Media 1 (1.5 μm superficially porous silica based C18)
Dimensions: 2.1×50 mm, 2.1×100 mm and 2.1×150 mm
Mobile Phase: MeCN/$H_2$O=50/50 (v/v)
Temperature: 30° C.
Flow Rate: 0.40 mL/min
Inj. Volume: 1 μL
Detection: UV (254 nm)
Sample Composition:
1. Theophylline (0.008 mg/mL
2. o-Nitroaniline (0.025 mg/mL)
3. Methyl Benzoate (0.18 mg/mL)
4. Phenetole (0.30 mg/mL)
5. o-Xylene (0.48 mg/mL)
Column: Media 2 (1.9 μm totally porous silica based C18)
Dimensions: 2.1×50 mm, 2.1×100 mm, 2.1×150-mm and 2.1×200-mm
Mobile Phase: MeCN/$H_2$O=50/50 (v/v)
Temperature: 30° C.
Flow Rate: 0.50 mL/min
Inj. Volume: 1 μL
Detection: UV (254 nm)
Sample Composition:
1. Theophylline (0.032 mg/mL
2. o-Nitroaniline (0.10 mg/mL)
3. Methyl Benzoate (0.71 mg/mL)
4. Phenetole (01.2 mg/mL)
5. o-Xylene (1.92 mg/mL)

The results of the column performance tests for the respective media are illustrated in FIGS. 3, 4a, 4b, 5, 6, 7a, and 7b.

Column Packing Robustness Evaluation (UHPLC Conditions Simulation)

Figure 2:
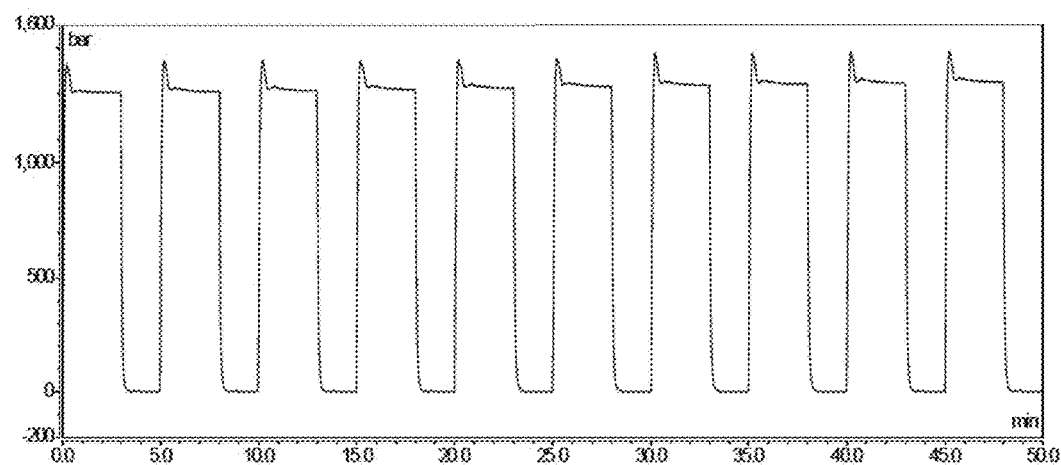
FIG. 2 shows a typical pressure trace for the column packing robustness test on a 100×2.1 mm column packed with Media 1 (1.5 µm superficially porous silica based C18) particles.

The column packing quality was assessed by the following method:

1. The column performance test was performed on a freshly packed column,
2. On a 1500-bar pressure rated UHPLC instrument, the column pressure was oscillated between 0 (held for 2 min) and 1500 bar (held for 3 min) for 100 cycles. FIG. 2 shows a typical pressure trace.
3. The column performance test was repeated.

The particular conditions for the robustness test were:
Column: Media 1 (superficially porous C18, 1.5 μm)
Dimension: 2.1×100 mm
Mobile Phase: 50/50 A:B
A: Water
B: Acetonitrile
Temperature: 30° C.
Sample: None
Inj. Volume: None
Detection: Pressure (bar)
Flow Rate: Each cycle 0.675 mL/min @ 1500 bar for 3 min,
0 mL/min @ 0 bar for 2 min
(100 cycles; 10 shown in FIG. 1)

FIG. 2 shows a typical pressure trace for the column packing robustness test on a 100×2.1 mm column packed with Media 1 (1.5 μm superficially porous silica based C18) particles.

Figure 3:
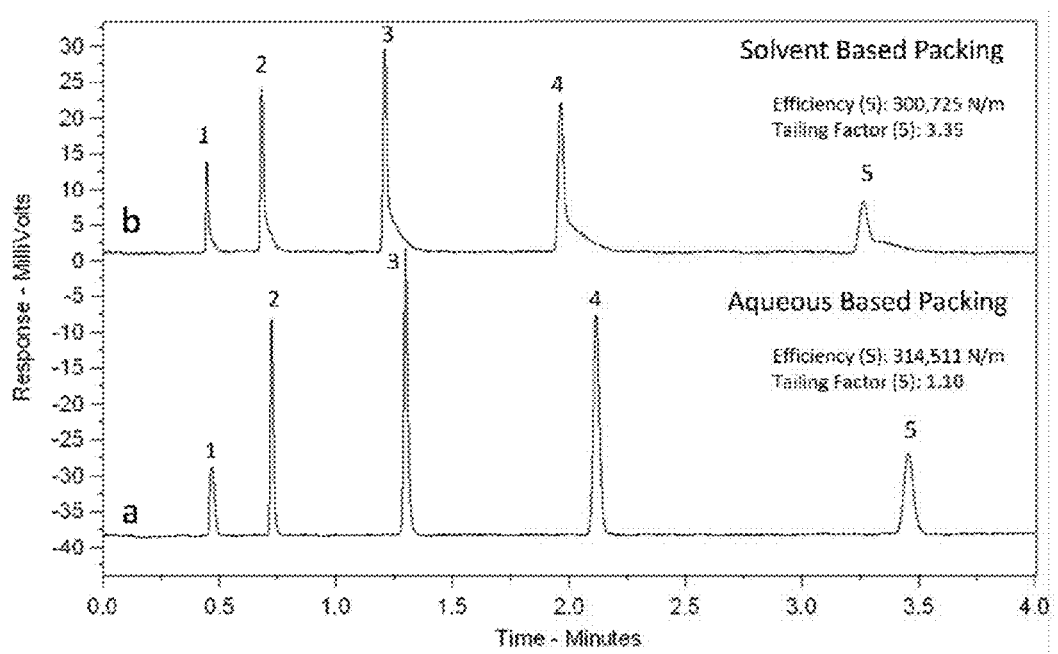
FIG. 3 shows a column performance comparison between two 100×2.1 mm columns packed with Media 1 (1.5 µm superficially porous silica based C18) particles at 2400 bar using both the aqueous based (chromatogram a) and solvent based packing methods (chromatogram b) of Examples 1 and 2. Note that chromatogram a was shifted downward on the y-axis for purpose of illustrating the relative differences in peak shape to chromatogram b.

FIG. 3 shows column performance comparison between the two 100×2.1 mm columns packed with Media 1 (1.5 μm superficially porous silica based C18) particles at 2400 bar using both the aqueous based and solvent based packing methods of Examples 1 and 2. It is evident that the aqueous packing method provides improved packing quality compared to the solvent packing where significant tailing is seen.

Figures 4A, 4B:
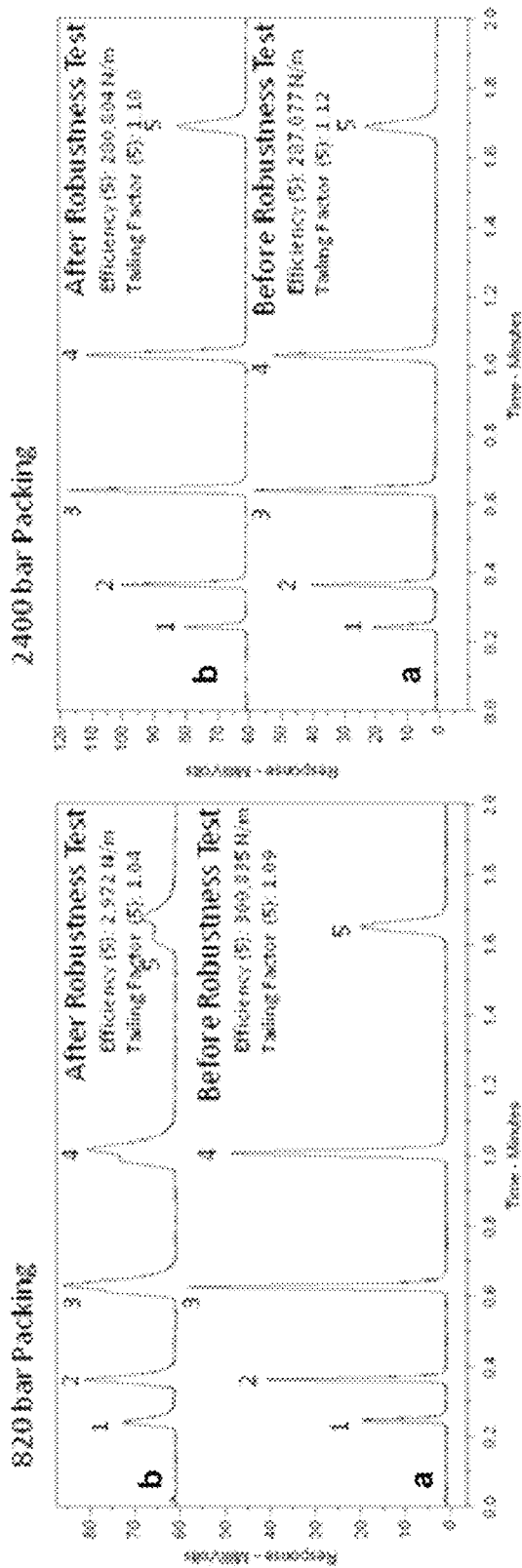

FIGS. 4a and 4b show column performance results before and after the robustness test on two 50×2.1 mm columns packed with Media 1 (1.5 μm superficially porous silica based C18) particles at 820 bar (Example 3 above) and 2400 bar (Example 4 above) using aqueous based packing methods. Although both columns exhibit good performance test results initially, the sequential robustness test reveals that the column packed with the consolidation step at higher pressure (2400 bar) yield superior column packing quality with less than 3% decrease in column efficiency vs. severe peak splitting for one-stage packing at lower pressure.

Figure 5:
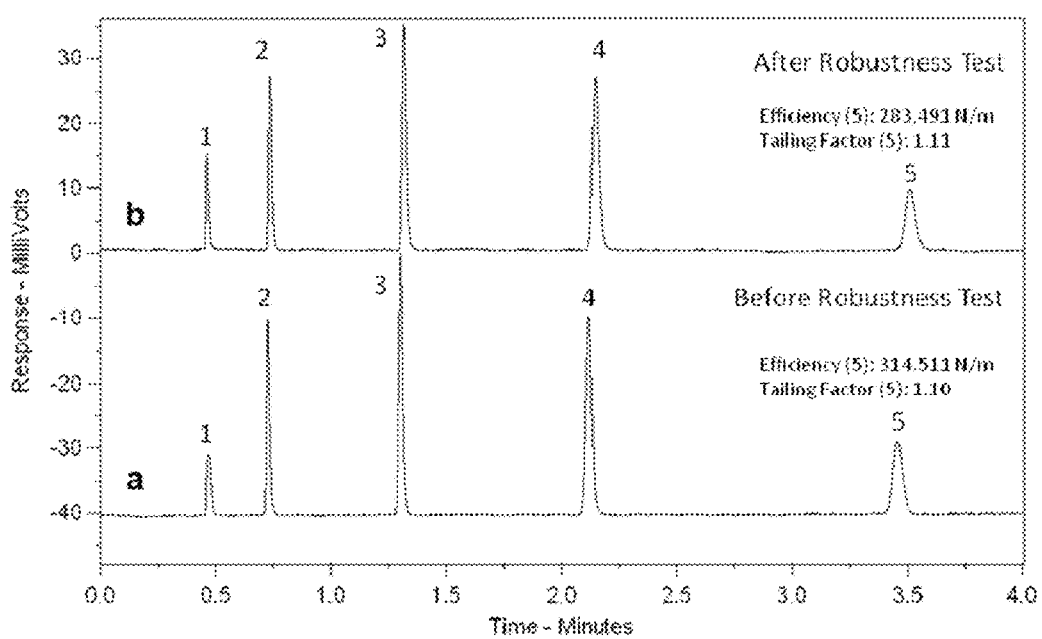
FIG. 5 shows column performance results before and after the robustness test (chromatogram a and chromatogram b, respectively) on a 100×2.1 mm column packed with Media 1 (1.5 µm superficially porous silica based C18) particles using the 2-stage aqueous based packing method at 2400 bar in Example 1. Note that chromatogram a was shifted downward on the y-axis for the purpose of comparing possible differences in peak shapes with chromatogram b.

FIG. 5 shows column performance results before and after the robustness test on a 100×2.1 mm column packed with Media 1 (1.5 μm superficially porous silica based C18) particles using the 2-stage aqueous based packing method at 2400 bar (Example 1 above). After fluctuating between 0 and 1500 bar for an extensive period of time, the column performance remains good (e.g., <10% decrease in efficiency).

Figure 6:
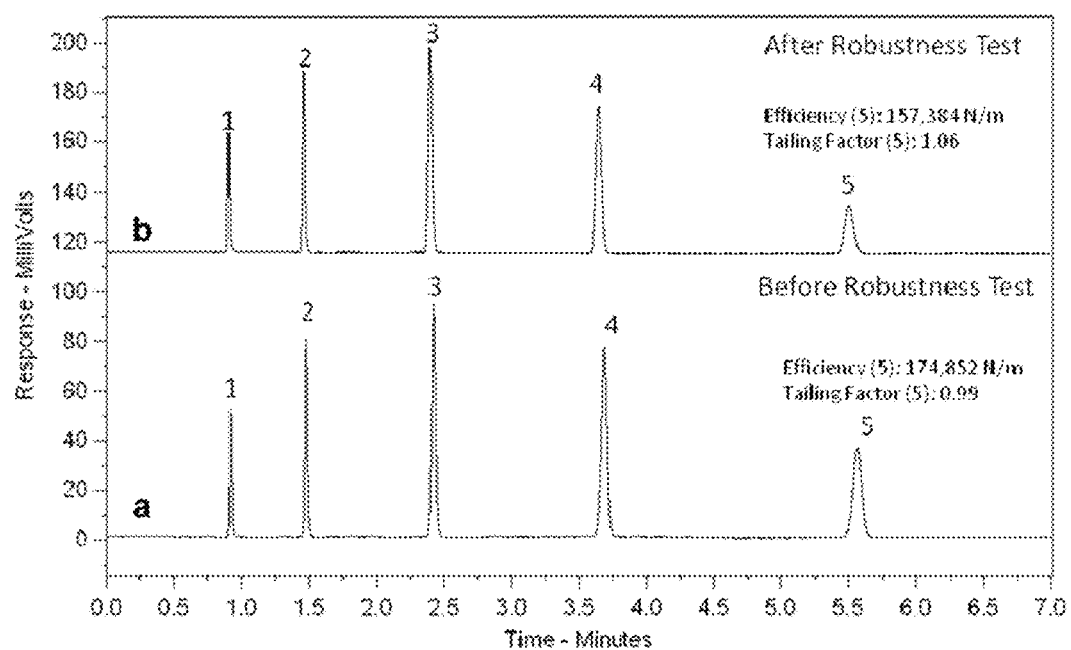

FIG. 6 shows column performance results before and after the robustness test on a 200×2.1 mm column packed with Media 2 (1.9 μm porous silica based C18) particles using a 2-stage aqueous based packing method at 2400 bar (Example 5 above). After fluctuating between 0 and 1500 bar for extensive period of time, the column performance remains good.

Figures 7A, 7B:
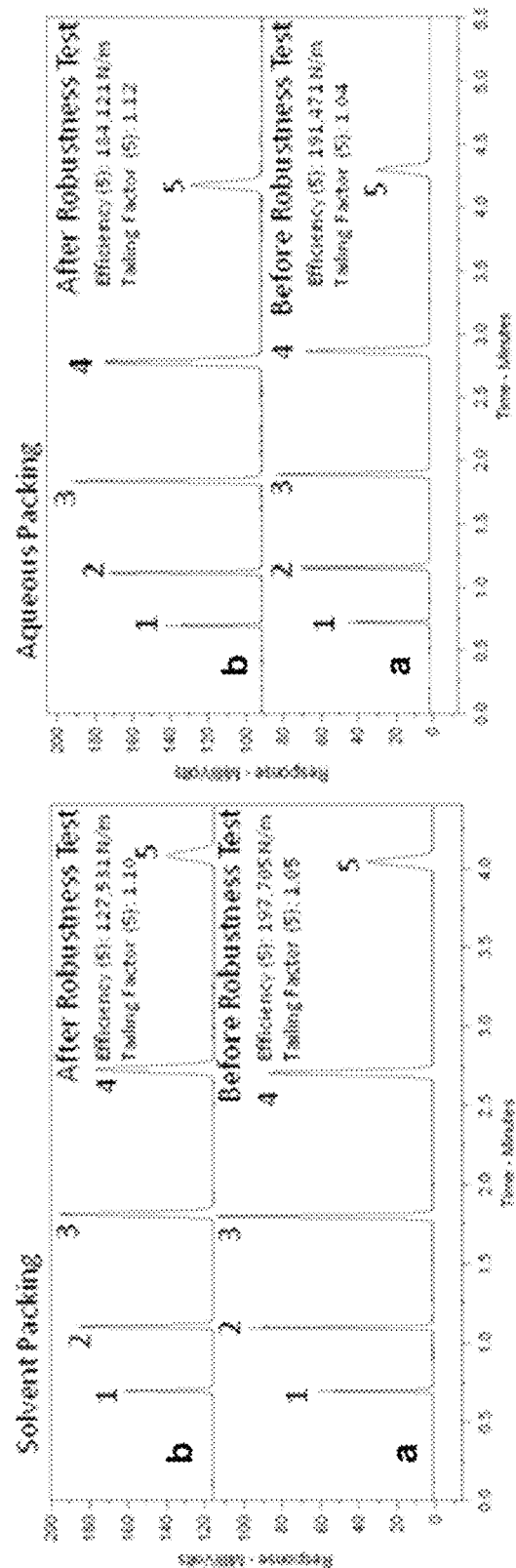

FIGS. 7a and 7b show column performance results before and after robustness testing on two 150×2.1 mm column packed with Media 2 (1.9 μm porous silica based C18) particles at 2400 bar using 2-stage solvent based (chromatograms a and b of FIG. 7a) and aqueous based packing methods (chromatograms a and b of FIG. 7b) (Examples 6 and 7, respectively). Although both columns exhibit good performance test results initially, the sequential robustness test revealed that the column packed with the aqueous packing method yielded superior column packing quality with less than 4% decrease in column efficiency compared to the column packed with the solvent packing (35% efficiency loss after robustness test).

Further experimental data is provided in table 1 below.

TABLE 1

| Column Dimensions (mm) | Packing Method | Robustness-Maximum Pressure (bar) | Efficiency (N/m) Before Robustness Testing | Tailing Factor (EP) Before Robustness Testing | Efficiency (N/m) After Robustness Testing | Tailing Factor After Robustness Testing | % Δ Efficiency | % Δ Tailing Factor |
|---|---|---|---|---|---|---|---|---|
| Superficially Porous C18, 1.5 μm | | | | | | | | |
| 2.1 × 50 | Aqueous, 800 bar | 1000 | 300,835 | 1.09 | 2,972 | 1.04 | −99.0% | −4.6% |
| 2.1 × 50 | Aqueous, 2400 bar | 1000 | 287,077 | 1.12 | 280,804 | 1.10 | −2.2% | −1.8% |
| 2.1 × 50 | Solvent, 2400 bar | 1000 | 300,835 | 1.09 | 2,972 | 1.04 | −99.0% | −4.6% |
| 2.1 × 100 | Aqueous, 2400 bar | 1500 | 314,511 | 1.10 | 283,491 | 1.11 | −9.9% | 0.9% |
| 2.1 × 100 | Solvent, 2400 bar | 1500 | 300,725 | 3.35 | 32,233 | 1.24 | −89.3% | −63.0% |
| 2.1 × 150 | Aqueous, 2400 bar | 1500 | 305,480 | 0.99 | 283,491 | 1.11 | −7.2% | 12.1% |
| 2.1 × 150 | Solvent, 2400 bar | 1500 | 266,767 | 3.92 | N/A | N/A | N/A | N/A |
| Totally Porous C18, 1.9 μm | | | | | | | | |
| 2.1 × 150 | Aqueous, 2400 bar | 1500 | 191,471 | 1.04 | 184,121 | 1.12 | −3.8% | 7.7% |
| 2.1 × 150 | Solvent, 2400 bar | 1500 | 197,705 | 1.05 | 127,531 | 1.10 | −35.5% | 4.8% |
| 2.1 × 200 | Aqueous, 2400 bar | 1500 | 174,852 | 0.99 | 158,384 | 1.07 | −9.2% | 8.1% |
| 2.1 × 200 | Solvent, 2400 bar | 1500 | 179,843 | 1.02 | 119,983 | 1.04 | −33.3% | 2.0% |

It can be seen from the above description that the invention can be provided in accordance with the following numbered clauses:

A method of packing a chromatography column, including:

dispersing chromatographic media particles in an aqueous based slurry solution to form a slurry;

filling a chromatography column with the chromatographic media particles by introducing the slurry to the column; and applying a pressure to pack the chromatographic media particles in the chromatography column.

The method of clause i wherein the aqueous based slurry solution is 100% water, or at least 90%, or at least 95%, or at least 99%, by weight water.

The method of any preceding clause wherein the aqueous based slurry solution contains organic solvent(s) in an amount not more than 100 parts by weight, not more than 50 parts by weight, or not more than 40 parts by weight, or not more than 30 parts by weight, or not more than 20 parts by weight, or not more than 10 parts by weight, or not more than 5 parts by weight, or not more than 1 part by weight organic solvent(s), based on 100 parts by weight of water.

The method of any preceding clause wherein the aqueous based slurry solution further includes, based on 100 parts by weight of water:
0-50, or 0-40, or 0-30, or 0-20 or 0-10 or 0-5 or 0-1, parts by weight of surfactant;
0-50, or 0-40, or 0-30, or 0-20 or 0-10 or 0-5 or 0-1, parts by weight of electrolyte or salt (other than ionic surfactant);
0-100, or 0-50, or 0-30, or 0-20 or 0-10 or 0-5 or 0-1, parts by weight of acid; and
0-100, or 0-50, or 0-30, or 0-20 or 0-10 or 0-5 or 0-1, parts by weight of base.

The method of any preceding clause wherein the applied pressure includes a pressure of at least 500 bar, or at least 800 bar, or at least 1000 bar, or at least 1300 bar, or at least 1500 bar, or at least 2000 bar for a period of time.

The method of any preceding clause wherein the pressure is applied and held substantially constant for a first period at a first pressure and is applied and held substantially constant for a second period, following the first period, at a second pressure higher than the first pressure.

The method of any preceding clause wherein the first pressure is in a range from 100-1500 bar, or 100-1300 bar, or 100 to 1000 bar, or 300 to 1000 bar, or 500 to 1000 bar; and the second pressure is in a range from 1500 to 6000 bar, or 1500 to 5000 bar, or 1500 to 4000 bar, or 1500 to 3000 bar.

The method of any preceding clause wherein the first pressure is in a range from 100-1500 bar; and the second pressure is in a range from 1500 to 4000 bar or 1500 to 4000 bar.

The method of any preceding clause wherein the first period is in a range from 0.1-100 hours, or 0.2 to 50 hours and the second period is in a range from 0.1-100 hours, or 0.2 to 50 hours.

The method of any preceding clause wherein the column has an internal diameter from 10 μm to 5 mm, or from 100 μm to 5 mm; and the column has a length from 20 mm to 10,000 mm, or from 20 mm-1,000 mm.

The method of any preceding clause wherein the chromatographic media particles have a median particle diameter of 1 to 5 μm and are totally porous or superficially porous.

A method of packing a chromatography column, including:
dispersing chromatographic media particles in a slurry solution to form a slurry;
filling a chromatography column with the chromatographic media particles by introducing the slurry to the column; and
applying a pressure to pack the chromatographic media particles in the chromatography column, wherein the pressure is applied and held substantially constant for a first period at a first pressure and is applied and held substantially constant for a second period, following the first period, at a second pressure higher than the first pressure.

The method of clause xii wherein the first pressure is in a range from 100-1500 bar, or 100-1300 bar, or 100 to 1000 bar, or 300 to 1000 bar, or 500 to 1000 bar; and the second pressure is in a range from 1500 to 6000 bar, or 1500 to 5000 bar, or 1500 to 4000 bar, or 1500 to 3000 bar.

The method of any clause xii to xiii wherein the first pressure is in a range from 100-1500 bar; and the second pressure is in a range from 1500 to 4000 bar or 1500 to 3000 bar.

The method of any clause xii to xiv wherein the first period is in a range from 0.1-100 hours and the second period is in a range from 0.1-100 hours The method of any clause xii to xv wherein the column has an internal diameter from 10 μm to 5 mm, or from 100 μm to 5 mm; and the column has a length from 20 mm to 10,000 mm, or from 20 mm-1,000 mm.

The method of any clause xii to xvi wherein the chromatographic media particles have a median particle diameter of 1 to 5 μm and are totally porous or superficially porous.

A liquid chromatography column for operation at liquid pressures of at least 500 bar, or at least 1000 bar, or at least 1300 bar or at least 1500 bar, wherein chromatographic media particles have been packed into the column from an aqueous based slurry solution.

The liquid chromatography column of clause xviii wherein chromatographic media particles have been packed into the column from the aqueous based slurry solution under an applied pressure that is substantially constant for a first period at a first pressure and is and held substantially constant for a second period, following the first period, at a second pressure higher than the first pressure.

A liquid chromatography column for operation at liquid pressures of at least 500 bar, or at least 1000 bar, or at least 1300 bar or at least 1500 bar, wherein chromatographic media particles have been packed into the column from a slurry solution under an applied pressure that is substantially constant for a first period at a first pressure and is and held substantially constant for a second period, following the first period, at a second pressure higher than the first pressure.

The liquid chromatography column of any clause xviii to xx wherein the column efficiency (Number of theoretical plates per meter, N/m) changes by less than 10% after a pressure applied to the column is oscillated between 0 bar for 2 min and 1500 bar for 3 min 100 times.

The liquid chromatography column of any clause xviii to xxi wherein the peak tailing factor changes (increases) by less than 15% after a pressure applied to the column is oscillated between 0 bar for 2 min and 1500 bar for 3 min 100 times.

The liquid chromatography column of any clause xviii to xxii wherein the backpressure changes (increases) by less than 10% after a pressure applied to the column is oscillated between 0 bar for 2 min and 1500 bar for 3 min 100 times.

As used herein, including in the claims, unless the context indicates otherwise, singular forms of the terms herein are to be construed as including the plural form and vice versa. For instance, unless the context indicates otherwise, a singular reference, such as "a" or "an" means "one or more".

Throughout the description and claims of this specification, the words "comprise", "including", "having" and "contain" and variations of the words, for example "comprising" and "comprises" and "etc." mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

The use of any and all examples, or exemplary language ("for instance", "such as", "for example", "e.g." and like language) provided herein, is intended merely to better illustrate the invention and does not indicate a limitation on the scope of the invention unless otherwise claimed. No language in the specification should be construed as indicating any non-claimed element as essential to the practice of the invention.

Any steps described in this specification may be performed in any order or simultaneously unless stated or the context requires otherwise.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

What is claimed is:

1. A method of packing a chromatography column, comprising:
    dispersing chromatographic media particles in an aqueous based slurry solution comprising at least 90% by weight water to form a slurry, wherein the aqueous based slurry comprises 0.1-10 parts by weight of surfactant based on 100 parts by weight of water;
    filling a chromatography column with the chromatographic media particles by introducing the slurry to the column; and
    applying a pressure to pack the chromatographic media particles in the chromatography column,
    wherein the pressure is applied and held substantially constant for a first period at a first pressure in a range from 100 to 1500 bar, and is applied and held substantially constant for a second period, following the first period, at a second pressure in a range from 1500 to 6000 bar.

2. The method of claim 1, wherein the aqueous based slurry solution further comprises, based on 100 parts by weight of water:
    0-10 parts by weight of electrolyte or salt;
    0-10 parts by weight of acid; and
    0-10 parts by weight of base,
    wherein at least one of the electrolyte or salt, the acid, and the base is present in an amount greater than 0 parts by weight.

3. The method of claim 1, wherein the first pressure is in a range from 500 to 1500 bar.

4. The method of claim 1, wherein the second pressure is in a range from 1500 to 4000 bar.

5. The method of claim 1, wherein the first period is in a range from 0.1-100 hours and the second period is in a range from 0.1-100 hours.

6. The method of claim 1, wherein the column has an internal diameter from 10 μm to 5 mm; and the column has a length from 20 mm to 10,000 mm.

7. The method of claim 1, wherein the chromatographic media particles have a median particle diameter of 1 to 5 μm and are totally porous or superficially porous.

8. The method of claim 1, wherein the aqueous based slurry solution is at least 95% by weight water.

9. The method of claim 1, wherein the aqueous based slurry solution is at least 99% by weight water.

10. The method of claim 1, wherein the aqueous based slurry solution contains organic solvent(s) in an amount not more than 10 parts by weight, based on 100 parts by weight of water.

11. The method of claim 1, wherein the aqueous based slurry solution contains organic solvent(s) in an amount not more than 5 parts by weight, based on 100 parts by weight of water.

12. The method of claim 1, wherein the aqueous based slurry solution contains organic solvent(s) in an amount not more than 1 part by weight, based on 100 parts by weight of water.

* * * * *